United States Patent
Sasaki et al.

(10) Patent No.: US 7,255,688 B2
(45) Date of Patent: Aug. 14, 2007

(54) PULL-ON DISPOSABLE WEARING ARTICLE

(75) Inventors: Toru Sasaki, Kagawa-ken (JP); Yoshio Ono, Kagawa-ken (JP); Satoru Sakaguchi, Kagawa-ken (JP); Tomoko Sugito, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 11/135,367

(22) Filed: May 24, 2005

(65) Prior Publication Data

US 2005/0267431 A1    Dec. 1, 2005

(30) Foreign Application Priority Data

May 28, 2004    (JP)    .............................. 2004-159836

(51) Int. Cl.
*A61F 13/15* (2006.01)
(52) U.S. Cl. ................ 604/396; 604/394; 604/385.24; 604/385.25; 604/385.27; 604/385.3; 604/385.01
(58) Field of Classification Search ................ 604/390, 604/385.01, 386, 385.24, 385.25, 385.27, 604/396, 394; 2/464, 466, 400–408, 78.1–78.4
See application file for complete search history.

(56) References Cited

U.S. PATENT DOCUMENTS

| | | | | |
|---|---|---|---|---|
| 4,940,464 A | * | 7/1990 | Van Gompel et al. | 604/396 |
| 5,782,819 A | * | 7/1998 | Tanzer et al. | 604/385.04 |
| 6,210,386 B1 | * | 4/2001 | Inoue | 604/385.13 |
| 6,213,991 B1 | * | 4/2001 | Kling et al. | 604/385.01 |
| 6,387,083 B1 | * | 5/2002 | Suzuki | 604/385.01 |
| 6,626,879 B1 | * | 9/2003 | Ashton et al. | 604/385.03 |
| 6,905,488 B2 | * | 6/2005 | Olson | 604/389 |
| 6,994,697 B2 | * | 2/2006 | Shimada et al. | 604/385.13 |
| 2002/0026172 A1 | * | 2/2002 | Shimada et al. | 604/385.13 |
| 2003/0055394 A1 | * | 3/2003 | Gibbs | 604/389 |
| 2004/0111076 A1 | * | 6/2004 | Sayama et al. | 604/385.13 |
| 2005/0043698 A1 | * | 2/2005 | Otsubo et al. | 604/385.25 |

FOREIGN PATENT DOCUMENTS

| | | |
|---|---|---|
| JP | 1991-224559 | 10/1991 |
| JP | 1992-166150 | 6/1992 |
| JP | 1992-289201 | 10/1992 |
| JP | 1993-15552 | 1/1993 |
| JP | 1996-507699 | 8/1996 |
| JP | 09-038135 | 2/1997 |
| JP | 09-117468 | 5/1997 |
| JP | 09-117469 | 5/1997 |

* cited by examiner

*Primary Examiner*—Jacqueline F. Stephens
(74) *Attorney, Agent, or Firm*—Lowe Hauptman & Berner LLP

(57) ABSTRACT

A pull-on disposable wearing article has a first waist region and a second waist region. The first waist region is elastically stretch- and contractible in the transverse direction. The second waist region is formed with a pair of finger-grip zones which are non-stretchable in the transverse direction and an elastically stretch- and contractible middle zone. The finger-grip zones respectively have a dimension in a range of 10 to 100 mm as measured in the transverse direction and extend from a peripheral edge of the waist-hole to peripheral edges of the respective leg-holes, along a pair of bonded zones where transversely opposite side edges of the waist regions are bonded together. The middle zone extends between the finger-grip zones is elastically stretch- and contractible in the transverse direction.

23 Claims, 11 Drawing Sheets

FIG.11
step a
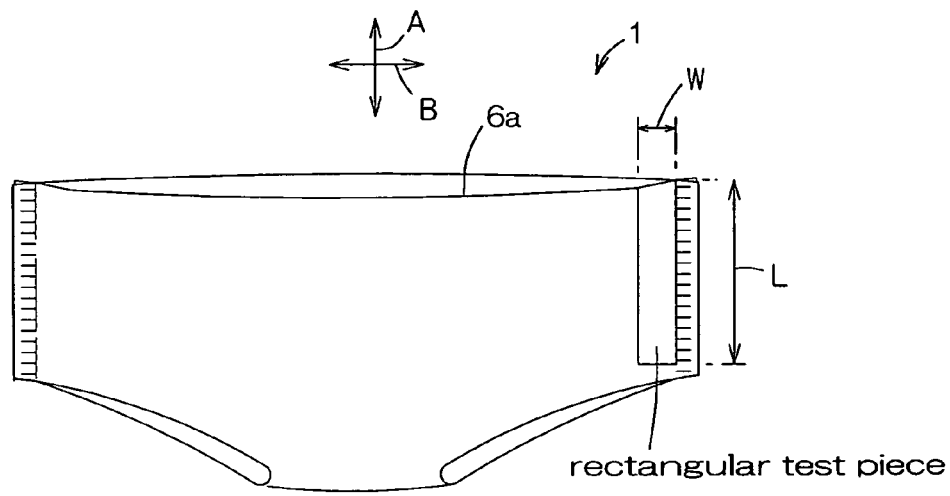
rectangular test piece
step b
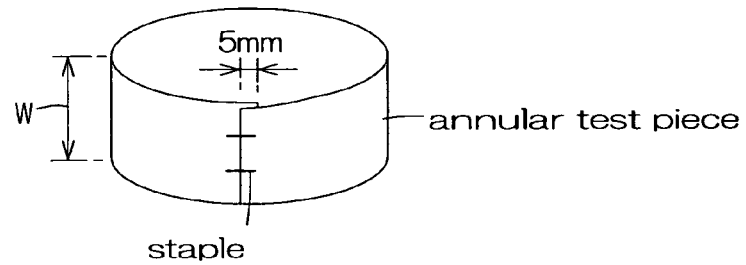
annular test piece
staple
step c
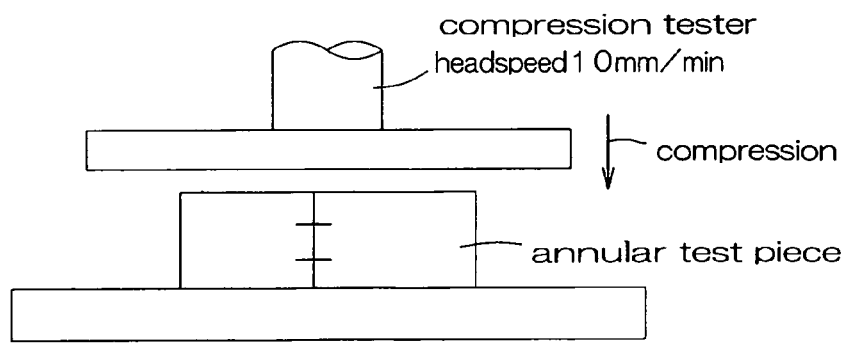
compression tester
headspeed 10mm/min
compression
annular test piece

PULL-ON DISPOSABLE WEARING ARTICLE

RELATED APPLICATIONS

The present application is based on, and claims priority from, Japanese Application Number 2004-159836, filed May 28, 2004, the disclosure of which is hereby incorporated by reference herein in its entirety.

BACKGROUND OF THE INVENTION

The present invention relates to a pull-on disposable wearing article such as disposable diaper, disposable training pants or the like.

It is well known to use pull-on wearing articles having a waist-hole and a pair of leg-holes, for example, as disposable diapers, training pants or diaper covers. It is also well known to make such wearing articles using woven or nonwoven fabrics and to attach elastic members in a stretched state to the articles along respective peripheral edges of the waist-hole and the leg-holes so that the articles may be put on a wearer's body with improved fit.

A pull-on disposable diaper disclosed in Japanese Unexamined Patent Application Publication No. 1992-166150 (Reference 1) as an example of such a wearing article includes, in addition to elastic members extending along peripheral edges of a waist-hole and leg-holes, elastic members attached in a stretched state to the article so as to extend across an absorbent pad and to make a full circle around the wearer's waist.

A disposable brief disclosed in Japanese Unexamined Patent Application Publication No. 1992-289201 (Reference 2) as another example of the foregoing wearing article includes a plurality of elastic members cooperating one with another to describe a loop extending around the wearer's waist.

A disposable diaper disclosed in Japanese Unexamined Patent Application (Based On Translated Version) Publication No. 1996-507699 (Reference 3) comprises a chassis having a front waist region, a rear waist region and a crotch region, and a pair of panels attached to the chassis each going half around the waist region and defining a waist-hole's peripheral edge and leg-holes' peripheral edges wherein the panels are elastically contractible in a waist-surrounding direction.

A pull-on disposable wearing article disclosed in Japanese Unexamined Patent Application Publication No. 1991-224559 (Reference 4) comprises an elastically stretchable topsheet formed from a nonwoven fabric, an elastically stretchable backsheet formed from a nonwoven fabric and elastic members extending along side edges of a crotch region and long respective upper ends of front and rear waist regions.

In a disposable pants disclosed in Japanese Unexamined Patent Application Publication No. 1993-15552 (Reference 5), a front waist region is formed from a transversely stretchable elastic sheet and a rear waist region is formed from a substantially inelastic sheet wherein the front waist region in a contracted state has a transverse dimension smaller than a transverse dimension of the rear waist region.

When a mother intends to put a pull-on diaper on her baby or when a care giver intends to put a pull-on diaper, for example, on a bedridden patient, mother or caregiver, in front of the baby or the bedridden patient, usually inserts both hands into the waist-hole of the diaper and grips transversely opposite side edges with the fingers to broaden the waist-hole. However, when a mother or caregiver intends to pull up the diaper after the wearer's legs have been let through the leg-holes, a peripheral edge of the waist-hole may get stuck on the wearer's buttock, preventing the diaper from being smoothly pulled up.

In the case of the diaper including the elastic member attached in a stretched state to the peripheral edge of the waist-hole, for example, as disclosed in References 1 and 2, portions of the waist-hole's peripheral edge is elastically stretched in the vicinity of portions gripped with the fingers when a mother or caregiver attempts to pull up the diaper getting stuck on the buttock. The peripheral edge of the waist-hole locally stretched in this manner may prevent the diaper from being smoothly pulled up.

In the diaper disclosed in Reference 3, transversely opposite lateral zones of the waist-hole are defined by the elastic panels. In this case also, when a mother or caregiver inserts both hands into the waist-hole of the diaper and grips transversely opposite lateral zones with the fingers to broaden the waist-hole and to pull up the diaper, the panels are elastically stretched in the vicinity of the portions gripped by the fingers, whether the diaper gets stuck on the wearer's buttock or not. Therefore, it may be difficult for a mother or caregiver to pull up the diaper smoothly.

Of the wearing article disposed in Reference 4, the front and rear waist regions are formed by the elastically stretchable top—and backsheets and these waist regions are provided along respective ends with the waist surrounding elastic members, respectively. For this reason, when it is intended to pull up the wearing article with the transversely opposite lateral zones of the waist-hole gripped by the fingers, the front and rear waist regions are stretched in the vicinity of the portions gripped by the fingers, possibly preventing the wearing article from being smoothly pulled up.

Of the disposable pants disclosed in Reference 5, the front waist region is formed from the transversely elastic sheet while the rear waist region is formed from the inelastic sheet and the front waist region has its transverse dimension smaller than the transverse dimension the rear waist region has. However, the elastic member comprising a plurality of elastic threads is attached in a stretched state to the waist-hole so as to make a full circle along the waist-hole. For this reason, when it is intended to pull up the pants by gripping the transversely opposite lateral zones of the waist-hole by the fingers, the lateral zones gripped by the fingers are elastically stretched as the peripheral edge of the waist-hole gets stuck on the wearer's buttock. Consequentially, it may be difficult for a mother or caregiver to pull up the pants smoothly.

All the known wearing articles including diapers are of pull-on and similar one to another in that the waist-hole is provided with the elastic member running a full circle along the peripheral edge thereof and when it is intended to pull up the wearing article, such elastic member may cause the wearing article to be stretched in the vicinity of the portions gripped by the fingers and thereby make it difficult to pull up the wearing article smoothly.

SUMMARY OF THE INVENTION

It is an object of the present invention to provide pull-on wearing articles improved to solve such a problem.

According to the present invention, there is provided a pull-on disposable wearing article comprising a first waist region, a second waist region and a crotch region extending between the first and second regions each having a longitudinal direction and a transverse direction orthogonal to the longitudinal direction, side edges of the first waist region opposed to each other in the transverse direction being bonded together with side edges of the second waist region opposed to each other in the transverse direction to form a pair of bonded zones extending in the longitudinal direction, a waist-hole, a pair of leg-holes, and the first and second waist regions being elastically stretch- and contractibly in the longitudinal direction and the transverse direction or at least in the transverse direction.

The present invention further comprises the first waist region being elastically stretch- and contractible over its full range in the transverse direction while the second waist region comprising a pair of finger-grip zones each extending from a peripheral edge of the waist-hole to one of peripheral edges of the leg-holes and vicinities thereof along the bonded zone over a range of 10 to 100 mm as measured from the bonded zone in the transverse direction and substantially non-stretchable in the longitudinal direction as well as in the transverse direction, and a middle zone defined between a pair of the finger-grip zones and being elastically stretch- and contractible over its full range in the transverse direction.

In accordance with the invention, the pull-on wearing article is formed in the first waist region with a pair of non-stretchable finger-grip zones each extending from a peripheral edge of the waist-hole to one of peripheral edges of the leg-holes and vicinites thereof. When it is intended to put this wearing article on the wearer's body, these finger-grip zones may be gripped by the fingers to pull the wearing article up along the wearer's body without an inconvenience that the wearing article might be stretched in vicinities of these fingers.

According to one preferred embodiment of the invention, a pair of the finger-grip zones is formed from a sheet material prepared separately from a sheet material used to form the middle zone.

According to such embodiment, the sheet material having color different from that of the sheet material used to form the zone other than the finger-grip zones may be used to distinguish the presence of the finger-grip zones.

According to another preferred embodiment of the invention, of the first waist region and the second waist region, zones other than the finger-grip zones comprise a nonwoven fabric composed of elastic fibers adapted to be elastically stretch- and contractible in the transverse direction and inelastic fibers describing a plurality of loops adapted to be straightened in the transverse direction so as to be elastically stretch- and contractible in the transverse direction.

According to such embodiment, both the first waist region and the second waist region except the finger-grip zones are formed from the nonwoven fabric which is elastically stretch- and contractible in the transverse direction and this nonwoven fabric comprises the elastic fibers and the inelastic fibers describing a plurality of loops adapted to be straightened in the transverse direction. When such nonwoven fabric is stretched in the transverse direction with the finger-grip zones gripped by the fingers of both hands, a force required to stretch the nonwoven fabric is relatively low until the loops of the inelastic fiber are completely straightened but, once the loops have been straightened, a relatively high force is required to stretch the nonwoven fabric since not only the elastic fibers but also the inelastic fibers constituting together the nonwoven fabric must be stretched. The diaper advantageously allows a mother or caregiver to perceive that the diaper can be no more easily stretched as the moment the loops have been completely straightened and, in response to this, a mother or caregiver can stop doing.

According to still another preferred embodiment of the invention, elastic members circularly extend along the peripheral edges of the leg-holes so that the elastic members are stretch- and contractible also in the finger-grip zones.

According to such embodiment, the peripheral edges of the leg-holes can be tightly pressed in a full circle against the wearer's thighs to prevent body fluid from leaking beyond these peripheral edges in spite of the presence of the non-stretchable finger-grip zones extending from the peripheral edge of the waist-hole to the peripheral edges of the leg-holes.

BRIEF DESCRIPTION OF THE DRAWINGS

FIG. 11 is a diagram illustrating sequential steps for measurement of flexural stiffness.

DETAILED DESCRIPTION OF THE PREFERRED EMBODIMENTS

Details of a pull-on disposable wearing article according to the present invention will be more fully understood from the description of a pull-on disposable diaper as an embodiment given hereunder with reference to the accompanying drawings.

Figure 1:
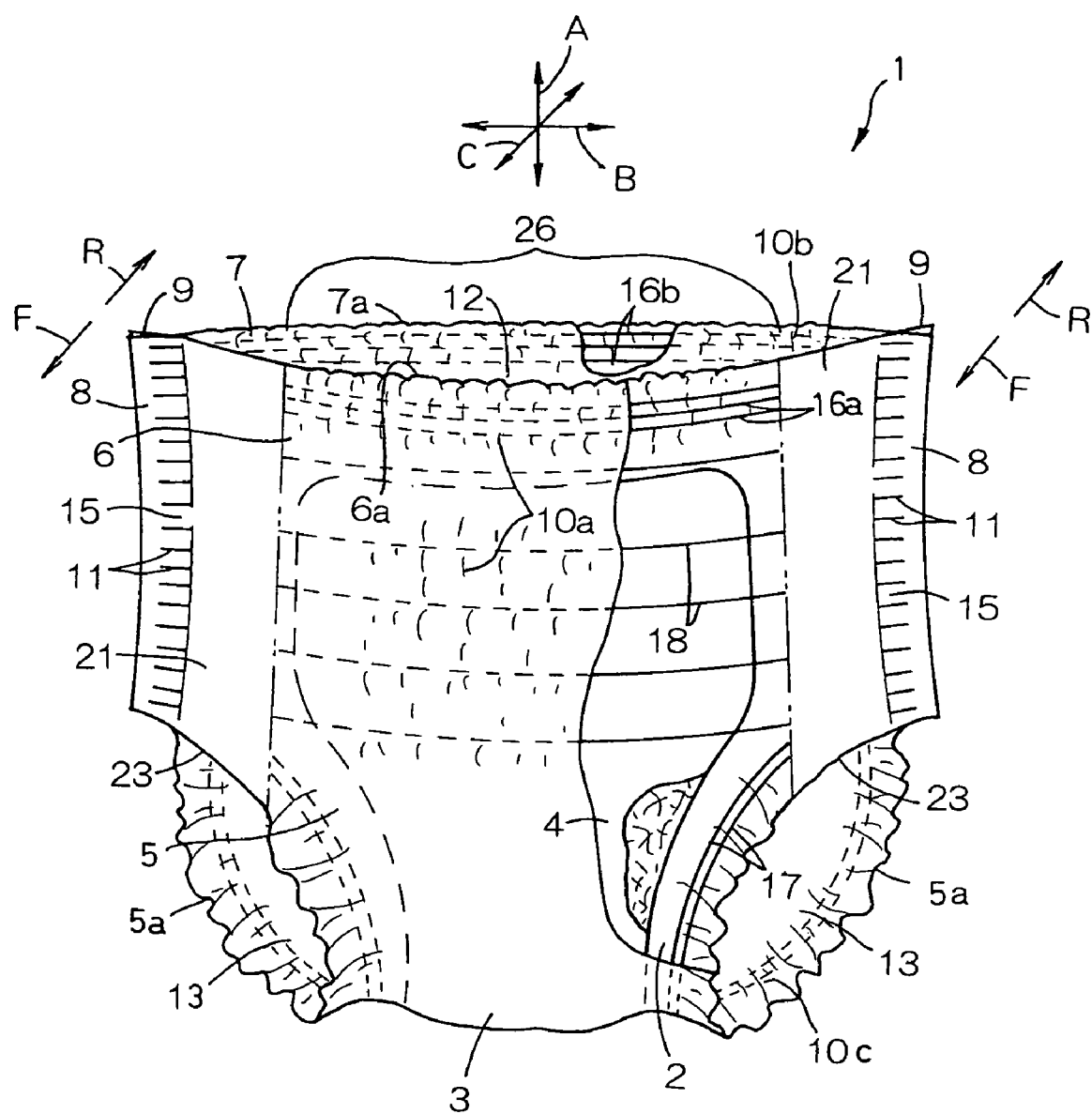
FIG. 1 is a partially cutaway perspective view showing a diaper.

As for materials, a pull-on disposable diaper 1 shown by FIG. 1 in a partially cutaway perspective view comprises a liquid-pervious inner sheet 2, a liquid-impervious outer sheet 3 and a body fluid absorbent core 4 interposed between these two sheets 2, 3 wherein portions of the inner and outer sheets 2, 3 extending outward beyond a peripheral edge of the core 4 are bonded together by means of hot melt adhesives (not shown). The diaper 1 has a front waist region 6, a rear waist region 7 and a crotch region 5 extending between these two waist regions 6, 7. In FIG. 1, a longitudinal direction of the front and rear waist regions 6, 7 is indicated by a double-headed arrow A, a transverse direction thereof is indicated by a double-headed arrow B and a thickness direction thereof is indicated by a double-headed arrow C. The front waist region 6 has a pair of side edges 8 opposite to each other in the transverse direction B so as to extend in the longitudinal direction A and the rear waist region 7 also has a pair of side edges 9 opposite to each other in the transverse direction B so as to extend in the longitudinal direction A. These side edges 8, 9 are bonded together by means of adhesives or welding technique at spots 11 arranged intermittently in the longitudinal direction A to form a pair of bonded zones 15. In the vicinity of an end 6a of the front waist region 6 and an end 7a of the rear waist region 7 defining together a peripheral edge of a waist-hole 12, a plurality of front waist elastic members 16a and a plurality of rear waist elastic members 16b extend along these ends 6a, 7a, respectively. In the vicinity of transversely opposite side edges 5a of the crotch region 5 forming peripheral edges of the respective leg-holes 13, a plurality of leg-surrounding elastic members 17 extend along the side edges 5a. These elastic members 16a, 16b, 17 are interposed between the inner and outer sheets 2, 3 and bonded in a stretched state to at least one of these sheets 2, 3. Across the front and rear waist regions 6, 7, a plurality of belly side auxiliary elastic members 18 and a plurality of back side auxiliary elastic members 19 extend in a stretched state, respectively (See FIG. 3). These auxiliary elastic members 18, 19 are interposed between the outer sheet 3 and the inner sheet 2 or between the outer sheet 3 and the core 4 and bonded to these inner and outer sheets 2, 3 and the core 4, preferably to the outer sheet 3 by means of hot melt adhesives (not shown). In such diaper 1, the front waist region 6 is formed with a pair of finger-grip zones 21 each extending along the bonded zones 15 from the end 6a of the front waist region 6 to the side edges 5a of the crotch region 5 which define peripheral edges of the respective leg-holes 13. The front waist elastic members 16a, the leg-surrounding elastic members 17 and the belly side auxiliary elastic members 18 are absent in the finger-grip zones 21. In the illustrated embodiment, the front waist elastic members 16a and the belly side auxiliary elastic members 18 are present only in a middle zone 26 of the front waist region 6 defined between a pair of the finger-grip zones 21 and the leg-surrounding elastic members 17 are present only in the crotch region 5 except the finger-grip zones 21.

Alternatively, the diaper 1 may comprise the inner sheet 2 and the outer sheet 3 formed from sheet materials such as nonwoven fabrics or plastic films which are non-stretchable in the longitudinal direction A as well as in the transverse direction B. The transversely middle zone 26 of the front waist region 6 and the entire rear waist region 7 are formed with gathers 10a, 10b as any one set of the elastic members 16a, 16b, 17, 18 contracts so that these zone 26 and region 7 are elastically stretch- and contractible in the transverse direction B, in other words, in a width direction of the diaper 1. Zones of the crotch region 5 extending along the side edges 5a and not included by the finger-grip zones 21 are formed with gathers 10c as the elastic members 17 contract so that these zones are elastically stretch- and contractible in the leg-surrounding direction. The finger-grip zones 21, on the other hand, includes none of these elastic members 16a, 17, 18 and are formed with none of gathers so that these finger-grip zones 21 are stretchable neither in the transverse direction B nor in the leg-surrounding direction.

Figure 2:
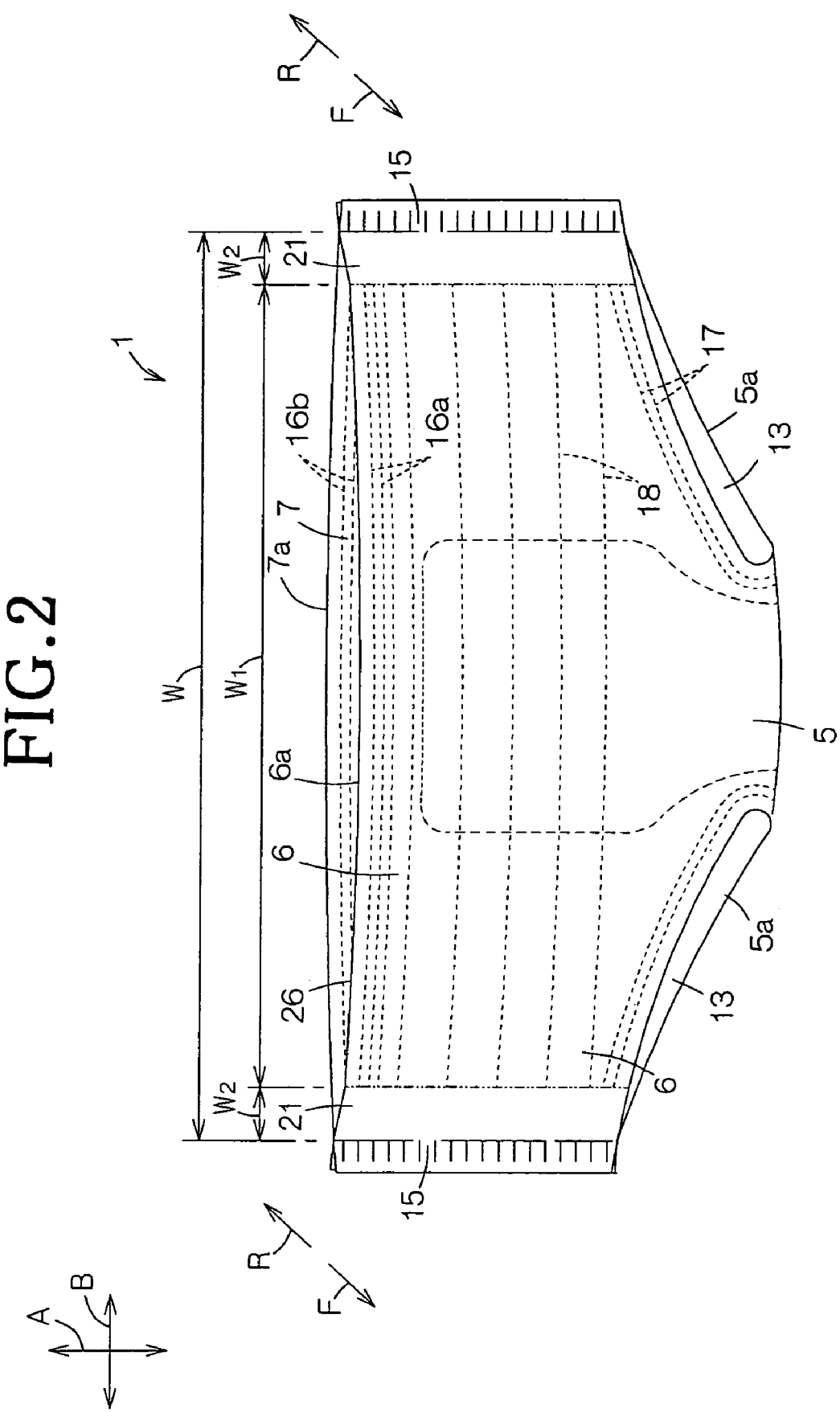
FIG. 2 is a front view showing the diaper of FIG. 1 as stretched in a longitudinal direction and in a transverse direction.
Figure 3:
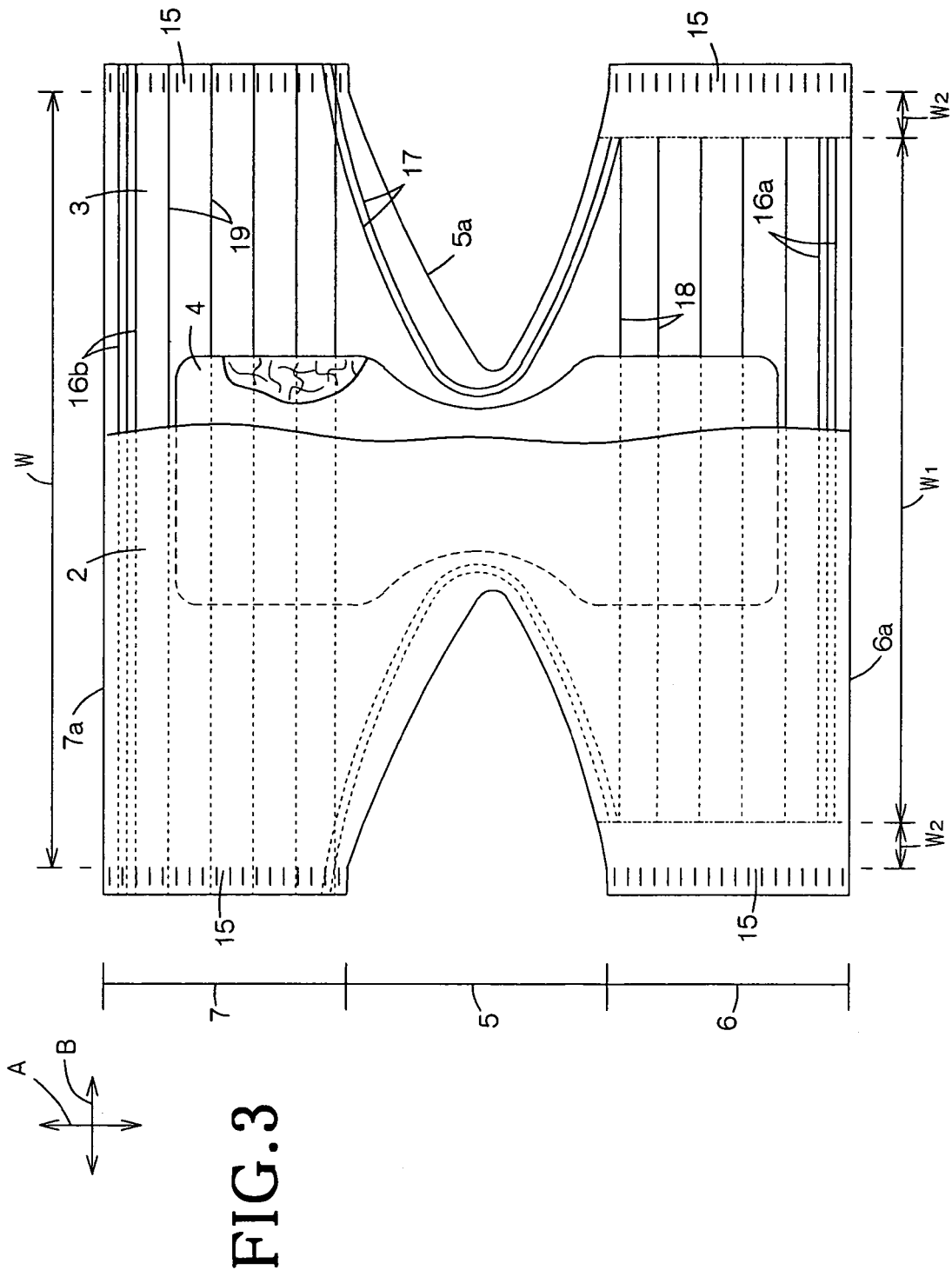
FIG. 3 is a partially cutaway plan view showing the diaper with front and rear waist regions disconnected from each other and developed in a back-and-forth direction.

FIG. 2 is a plan view showing the diaper 1 of FIG. 1 as stretched in the longitudinal direction A and in the transverse direction B with the elastic members 16a, 16b, 17, 18, 19 in stretched state and FIG. 3 is partially cutaway plan view showing the diaper 1 with the front and rear waist regions 6, 7 disconnected from each other along the bonded zones 15 and developed forward and rearward as indicated by arrows F, R. It should be noted that FIG. 2 shows the diaper 1 as slightly tilted forward in order that the end 6a of the front waist region 6 and the end 7a of the rear waist region 7 can be distinctly identified. In FIG. 3, the diaper 1 is shown with the inner sheet 2 facing the viewer. In FIGS. 2 and 3, a dimension in the transverse direction B (i.e., width) between the bonded zones 15, 15 in the front and rear waist regions 6, 7 is designated by W, a dimension in the transverse direction B of the middle zone 26 in the front waist region 6 is designated by $W_1$, a dimension in the transverse direction B of the finger-grip zone 21 is designated by $W_2$ and a dimension in the transverse direction B of the bonded zone 15 is in a range of 5 to 20 mm. The values of the dimensions W, $W_1$ largely depend on whether the diaper 1 is for infants or adults. While the values of the dimension $W_2$ also largely depend on whether the diaper 1 is for infant or adult, the value of $W_2$ in a range of 10 to 100 mm is preferable in order that the diaper 1 can be easily gripped by the fingers. The elastic members 16a, 16b, 17, 18, 19 may be attached to the diaper 1 generally with tension at a ratio of 20 to 300% so far as these elastic members 16a, 16b, 17, 18, 19 have a tensile stress as the typical elastic members used in the related art have. When the diaper 1 shown in FIGS. 1 and 2 is for infants, the diaper 1 may be dimensioned, for example, in a relationship of W=400 mm, $W_1$=360 mm and $W_2$=20 mm and the respective sets of elastic members 16a, 16b, 17, 18, 19 may be interposed between the inner sheet 2 and the outer sheet 3 or between the outer sheet 3 and the core 4 with tension preferably at a ratio of 20 to 300%, more preferably at a ratio of 50 to 200% so that a plurality of elastic members constituting the respective sets may extend in parallel one to another in the respective zones. The elastic members 16a, 16b, 17, 18, 19 interposed between the inner sheet 2 and the outer sheet 3 preferably exhibit a stress at 100% tension in a range of 0.1 to 5 N. "Stress at 100% tension as used here refers to the stress obtained as a result of a tensile test as follows: a single elastic member constituting each set of the elastic members is cut off over a length of 40 to 60 mm together with the inner sheet 2 and/or the outer sheet 3 from the diaper 1 in which the respective sets of elastic members 16a, 16b, 17, 18, 19 are left contract to prepare a tensile test piece; opposite ends of the tensile test piece are clamped by chucks of a tensile tester so as to leave an inter-chuck distance of 15 mm free; the tensile test piece is stretched at a rate of 200 mm/min; and a stress at the moment the inter-chuck distance is stretched to 30 mm is obtained as the stress at 100% tension.

Now it is assumed that the elastic members 16a, 16b, 17, 18, 19 are bonded with a 100% tension to the outer sheet 3 in the diaper 1 shown in FIGS. 2 and 3. It will be possible to let the dimension $W_1$ of the middle zone 26 in the front waist region 6 as well as the dimension W of the rear waist region 7 as shown in FIGS. 2 and 3 contract to approximately ½ $W_1$ and ½ W, i.e., to the order of $W_1$=180 mm and W=200 mm by appropriately selecting bonding conditions of the elastic members 16a, 16b, 17, 18, 19 and a stiffness of the inner and outer sheets 2, 3 so that contraction of these elastic members might not be significantly counteracted. In the diaper of FIG. 1 obtained in this manner, the dimension of the waist-hole 12 as measured in the transverse direction B will be in the order of 180 mm+(20 mm+20 mm)=220 mm and the dimension of the middle zone 26 as measured in the transverse direction B will be in the order of 200 mm.

Figure 4:
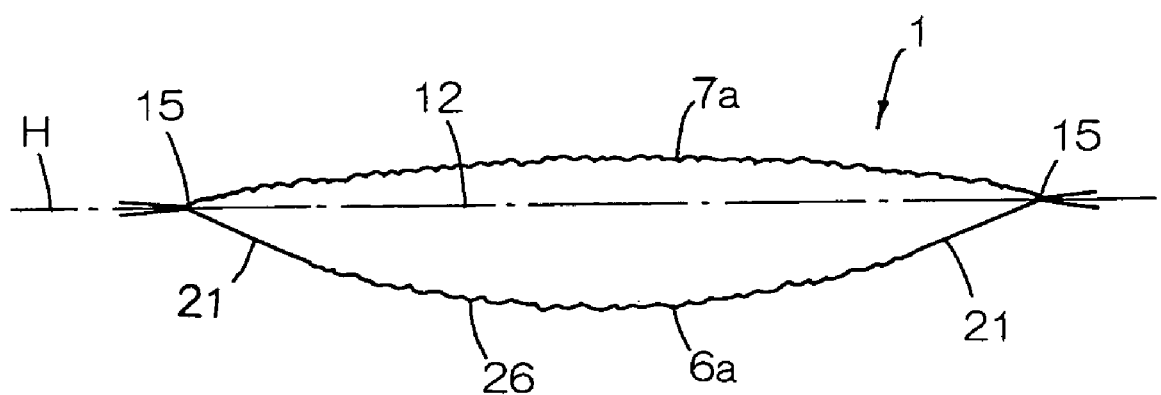
FIG. 4 is a diagram illustrating a shape described by upper edge of a waist-hole.

FIG. 4 schematically shows the respective ends 6a, 7a of the front and rear waist regions 6, 7 defining together the waist-hole 12 as viewed from the upper side of FIG. 1. In FIG. 4, the end 7a describing a circular arc above a horizontal line H is defined by a relatively long curvature radius and spaced from the horizontal line H by a correspondingly slight distance. On the other hand, the end 6a describing a circular arc below the horizontal line H is 20 mm longer than the end 7a and the finger-grip zones 21 slope down so that the middle zone 26 of the end 6a extending between these finger-grip zones 21 is spaced from the horizontal line H more significantly than the end 7a. In this manner, these ends 6a, 7a each in full length cooperate with each other to form the opening broadened downward. Specifically, the finger-grip zones 21 unshrinkably extending along the respective bonded zones 15 facilitate the waist-hole to be broadened.

The diaper 1 constructed in this manner facilitate a mother or caregiver to insert both hands into the waist-hole 12 because the waist-hole 12 is easily broadened. The middle zone 26 is no more stretched as the both hands are laterally spaced from each other by an appropriate distance, for example, approximately 360 mm. Consequently, the both hands are stabilized at the respective positions thus spaced from each other and the fingers of the both hands fall on the respective smooth finger-grip zones 21 formed in contiguity to the respective bonded zones 15 and having none of gathers on either surface thereof. Unlike the middle zone 26, the finger-grip zones 21 upon which the fingers fall are neither stretchable nor contractible and well stabilized in shape. Such feature facilitates a mother or caregiver to grip these zones 21. There is no anxiety that the finger-grip zones 21 might be stretched and slip off from the fingers as the diaper 1 is pulled up along the wearer's body with the finger-grip zones 21 by the fingers. Such feature facilitates the diaper 1 to be pulled up. With the diaper 1 of which the waist-hole 12 is in a state as shown in FIG. 4, even if the middle zone 26 of the front waist region 6 has been completely stretched in the transverse direction B in the course of pulling the diaper 1 up, the rear waist region 7 still has a possibility to be further stretched in the transverse direction B. Therefore, even if the rear waist region 7 gets stuck on the wearer's buttock in the course of pulling the diaper 1 up, the rear waist region 7 is further stretched to be pulled beyond the wearer's buttock. The finger-grip zones 21 functioning in the manner as has been described above in the vicinity of the waist-hole 12 preferably has a flexural stiffness higher than that of the intermediate zone extending between and contiguous to the finger-grip zones 21 in the transverse direction B and more preferably at least 1.5 times of the flexural stiffness of the intermediate zone. The flexural stiffness values of the finger-grip zones 21 and the intermediate zone extending between these finger-grip zones 21 are measured in the sequence as illustrated by FIG. 11. Referring to FIG. 11, in the step a), a rectangular test piece having a length L of 100 mm as measured downward from the end 6a of the waist-hole 12×a width W in the transverse direction B (without smoothing the gathers in the case of the diaper 1 having more or less gathers) of 10 to 30 mm is cut off from the diaper 1. In the step b), the rectangular test piece is rolled up in its longitudinal direction, then longitudinally opposite ends of this test piece are overlapped each other over 5 mm and this overlapped ends are stapled together at positions trisecting the width W to obtain an annular test piece. In the step c), a compression tester is used to compress this annular test piece in the width direction at a rate of 10 mm/min and to obtain the maximum load as the flexural stiffness. As measured using a test piece having a width of 30 mm, the preferred finger-grip zone 21 has a flexural stiffness in a range of 0.45 to 30 N corresponding to 1.2 times of the flexural stiffness exhibited by the intermediate zone or higher.

Figure 5:
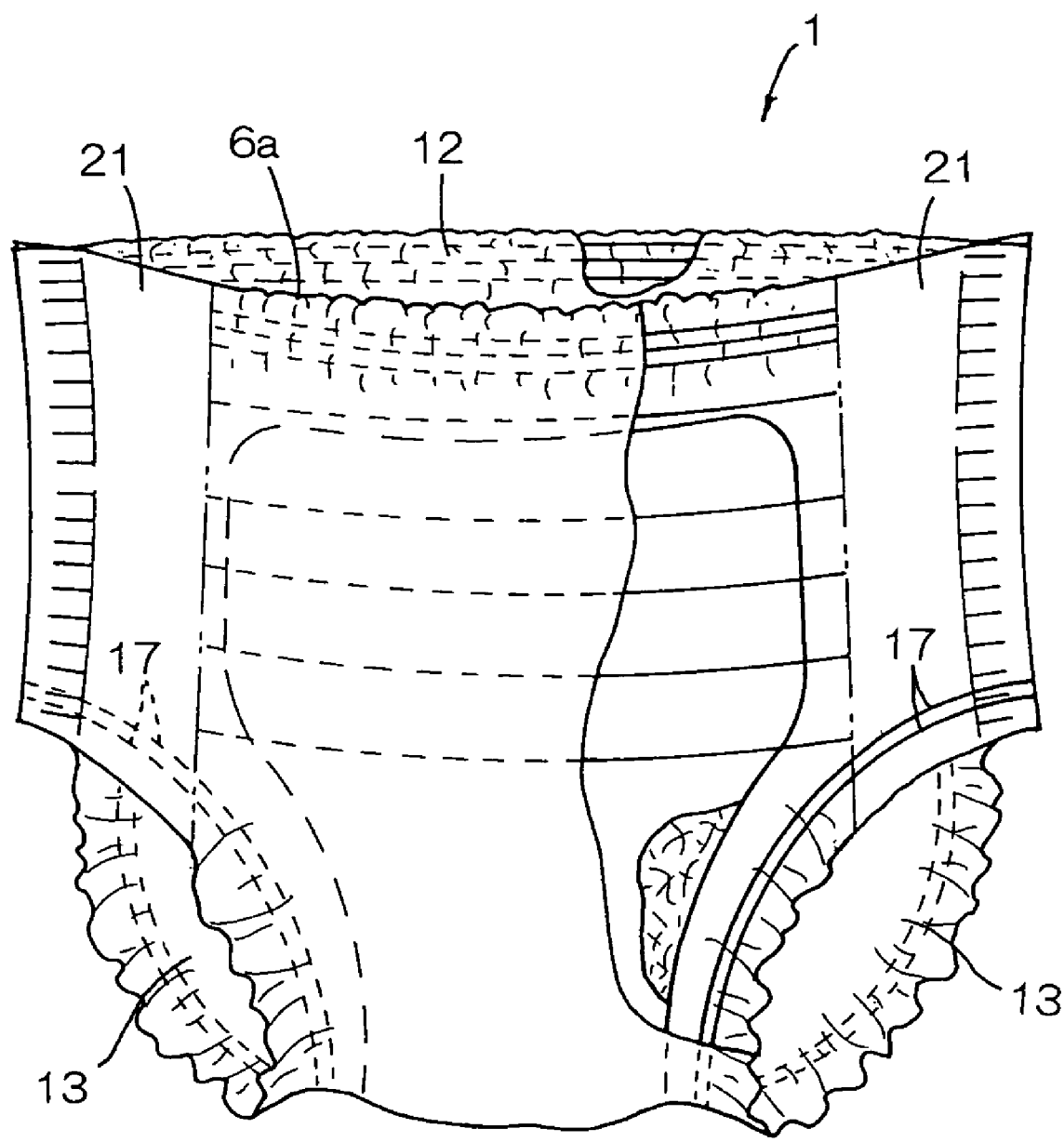
FIG. 5 is a view similar to FIG. 1, showing one preferred embodiment of the invention.

FIG. 5 is a view similar to FIG. 1, showing one preferred embodiment of the invention. In this diaper 1, the leg-surrounding elastic members 17 extend to the respective finger-grip zones 21 in a stretch- and contractible state to form rings which run full circles along the respective leg-holes 13. The leg-surrounding elastic members 17 in this diaper 1 can improve the protective effect against leakage of body fluids possibly occurring in the vicinity of the leg-holes without affecting the function expected for the finger-grip zones 21 which should facilitate the fingers to be inserted into the waist-hole 12 and to grip the front waist region 6 in the vicinity of its end 6a.

Figure 6:
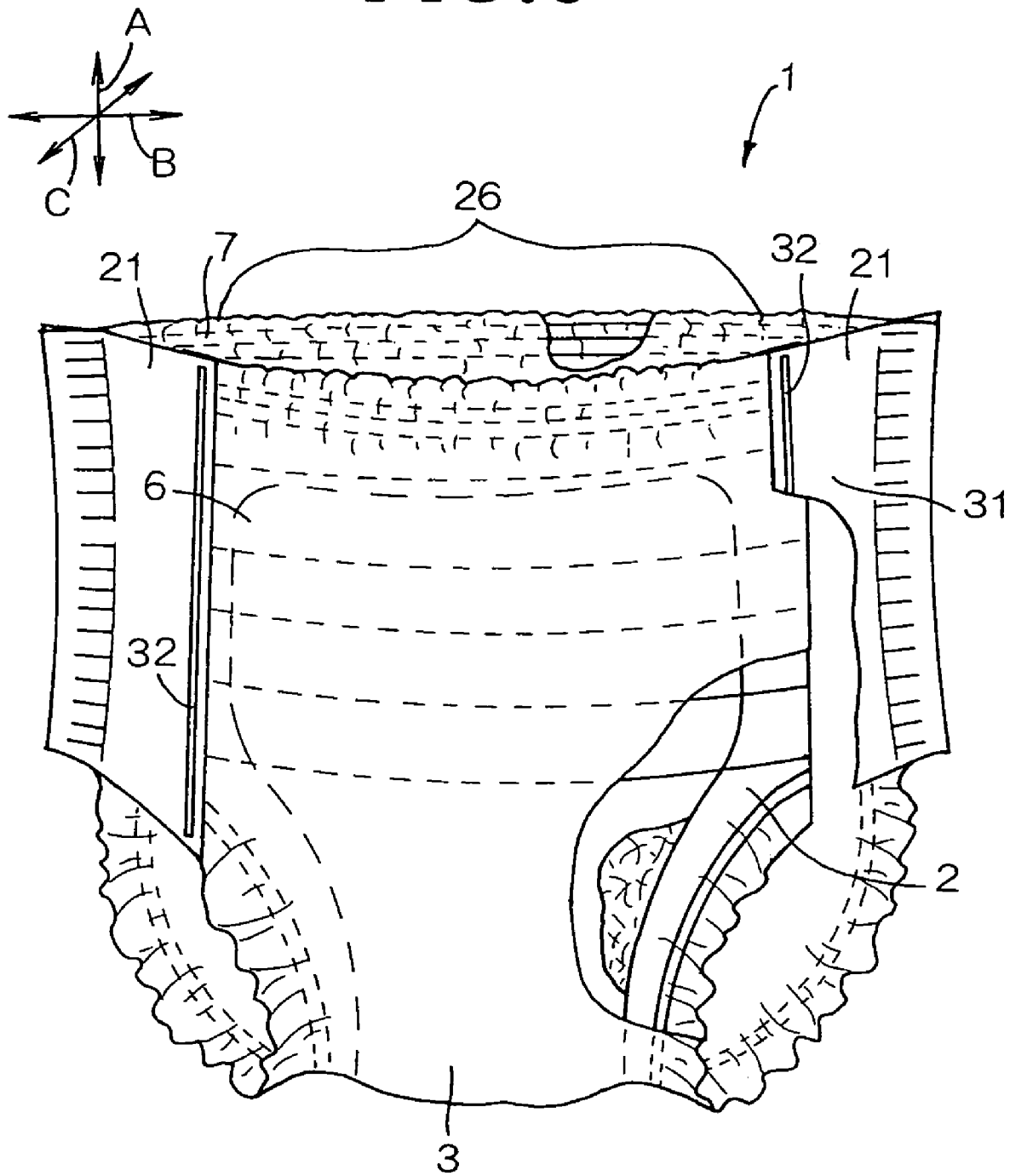
FIG. 6 is a view similar to FIG. 1, showing another embodiment of the invention.

FIG. 6 also is a view similar to FIG. 1, showing another embodiment of the invention. In this diaper 1, the finger-grip zones 21 are formed from a sheet material 31 prepared separately from the inner and outer sheets 2, 3 forming the middle zone 26. The sheet material 31 is non-stretchable in the longitudinal direction A as well as in the transverse direction, put flat with the inner and outer sheets 2, 3 and directly or indirectly bonded these sheets 2, 3 in a permanent manner along bonded lines 32 using adhesives or welding technique. The sheet material 31 having design and color different from those of the outer sheet 3 may be used to distinguish the presence of the finger-grip zones 21. In addition, the sheet material 31 having a flexural stiffness higher than that of segments of the middle zone 26 extending in the vicinity of the respective finger-grip zones 21 and comprising the inner and outer sheets 2, 3 put flat together with gathers may be used to facilitate a force exerted by the fingers on the finger-grip zones 21 to be transmitted to the middle zone 26 of the front waist region 6 and the rear waist region 7. The sheet material 31 is not limited to a woven fabric, nonwoven fabric and plastic film being used independently but may be a laminate thereof.

Figure 7:
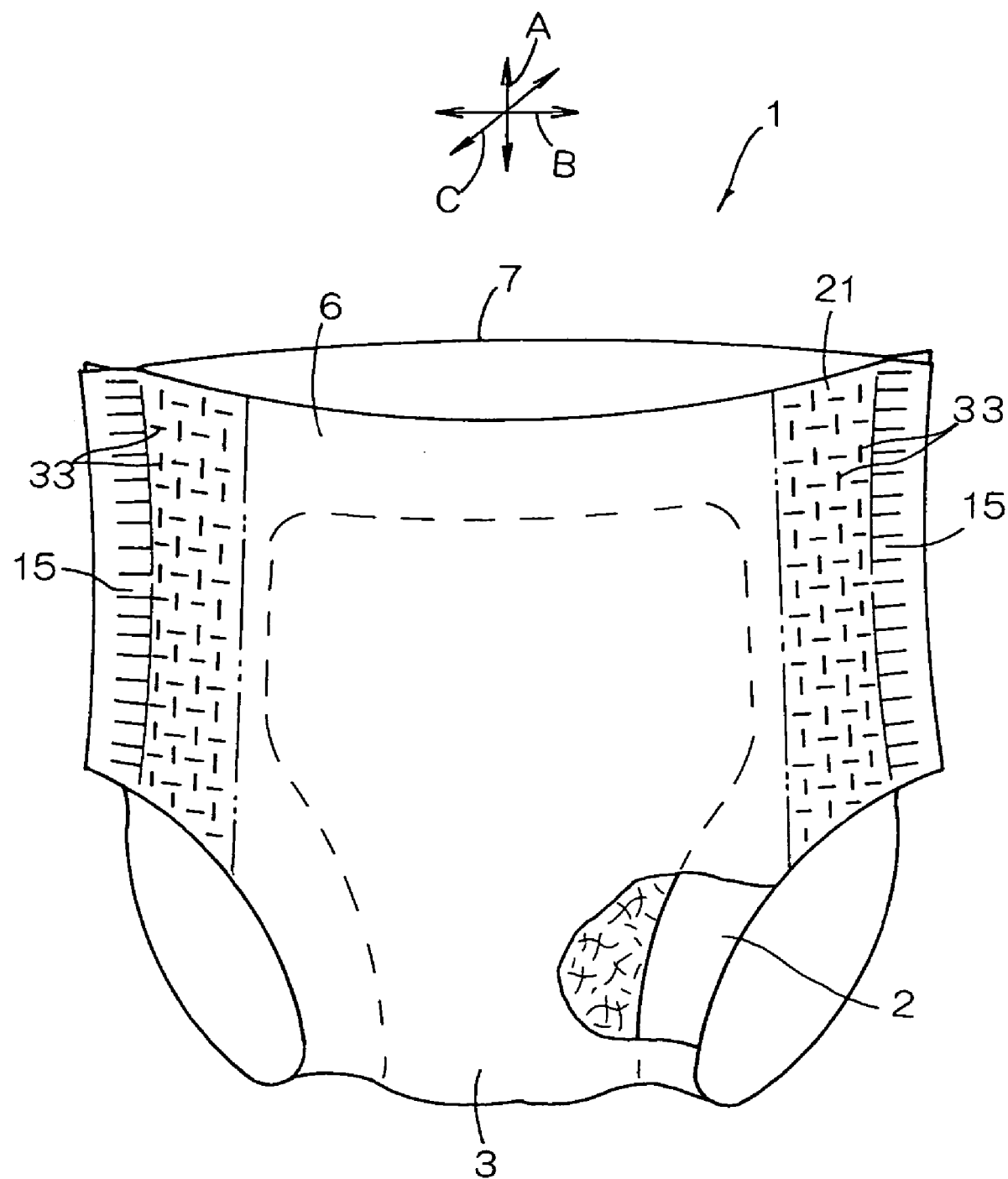
FIG. 7 is a view similar to FIG. 1, showing still another embodiment of the invention.

FIG. 7 also is a view similar to FIG. 1, showing still another embodiment of the invention. In this diaper 1, the inner and outer sheets 2, 3 are stretch- and contractible in the longitudinal and transverse directions A, B or at least in the transverse direction B and, in the finger-grip zones 21, at least one of the inner and outer sheets 2, 3 has its intrinsic elastic property suppressed and can be stretched neither in the longitudinal direction A nor in the transverse direction B. The inner sheet 2 may be formed from a nonwoven fabric made of elastic fibers such as urethane fibers, or a nonwoven fabric comprising the elastic fibers and inelastic fibers of polypropylene or the like describing a plurality of loops and mixed in this state with the elastic fibers. When the latter nonwoven fabric is stretched in the transverse direction, a force required to stretch the nonwoven fabric is relatively low until the loops of the inelastic fiber are completely straightened but, once the loops have been straightened, a relatively high force is required to stretch the nonwoven fabric since not only the elastic fibers but also the inelastic fibers constituting together the nonwoven fabric must be stretched. The diaper 1 using the nonwoven fabric of such behavior advantageously allows a mother or caregiver to perceive that it is no more easy to stretch the diaper 1 can be no more easily stretched as the moment the loops have been completely straightened. Stock materials for the outer sheet 3 is not limited to the body fluid impervious film which is made of an elastomer such as a urethane and elastically stretchable but the nonwoven fabric may be formed also from the laminate of the elastic fibers and the inelastic fibers which have been described as an example of the stock material for the inner sheet 2 and allows a mother or caregiver to perceive the stretchable limit of the diaper 1. The zone defined by the inner and outer sheets 2, 3 placed upon each other and being elastically stretch- and contractible in the transverse direction B preferably has a tensile stress in a range of 0.2 to 1 N/cm as measured by a testing method as follows: a test piece having a width of 1 cm and an inter-chuck distance of 15 mm is stretched at an inter-chuck stretching rate of 200 mm/min and a stretch stress value at the moment the test piece has been stretched by 50%. In the non-stretchable finger-grip zones 21, the elastic fiber and the inelastic fiber of the inner sheet 2 and/or the outer sheet 3 may be heated under a pressure at a plurality of spots 33 to form a plurality of inter-fibers fused spots or to convert these fibers to film-like state in an area as large as possible. In this way, the elastic property intrinsic to these sheets 2, 3 can be substantially suppressed. Alternatively, an inelastic sheet may be bonded to the elastic inner sheet 2 or the elastic outer sheet 3 using adhesives or welding technique to obtain the inelastic finger-grip zones 21.

Figure 8:
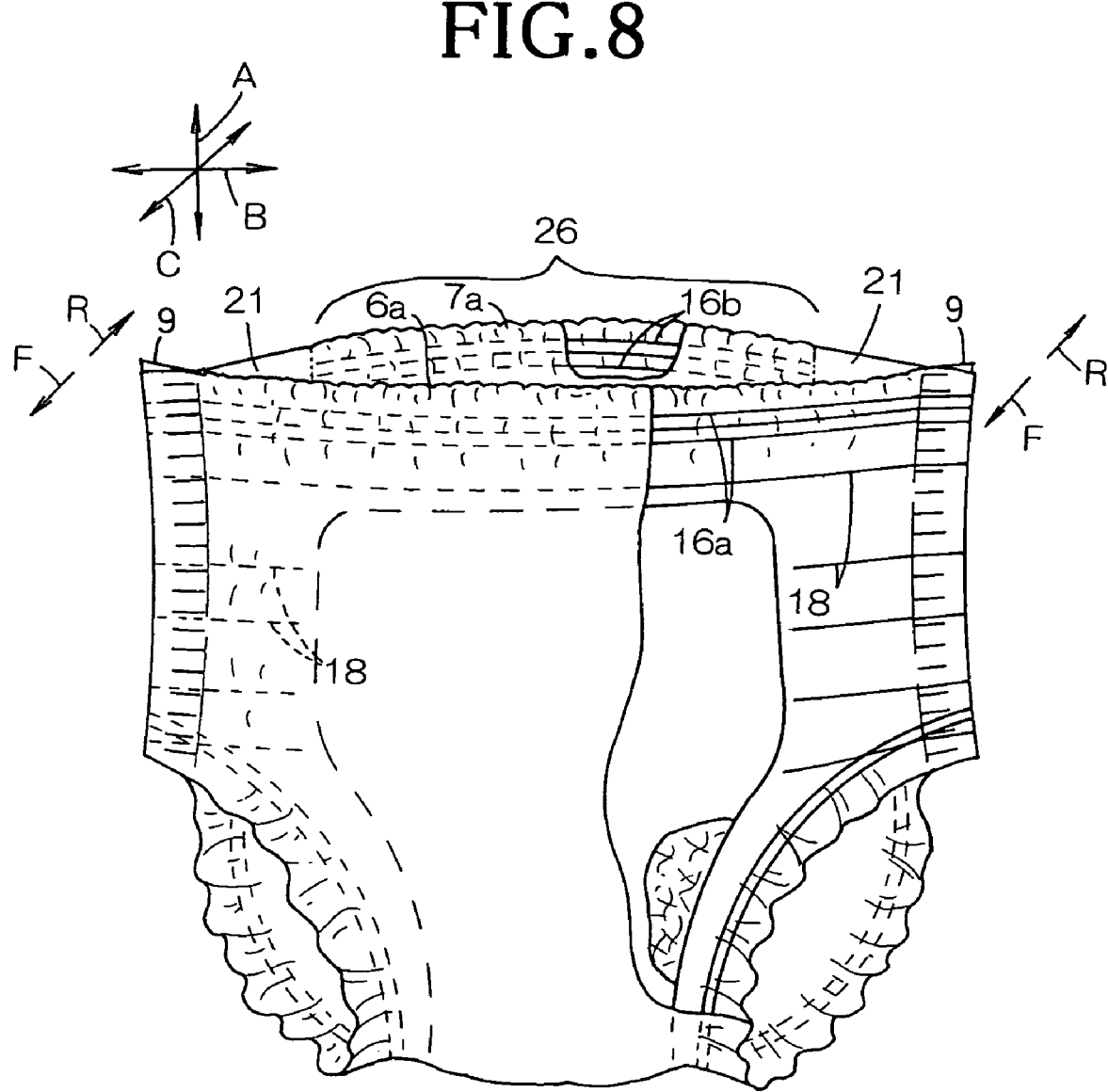
FIG. 8 is a view similar to FIG. 1, showing further another embodiment of the invention.
Figure 9:
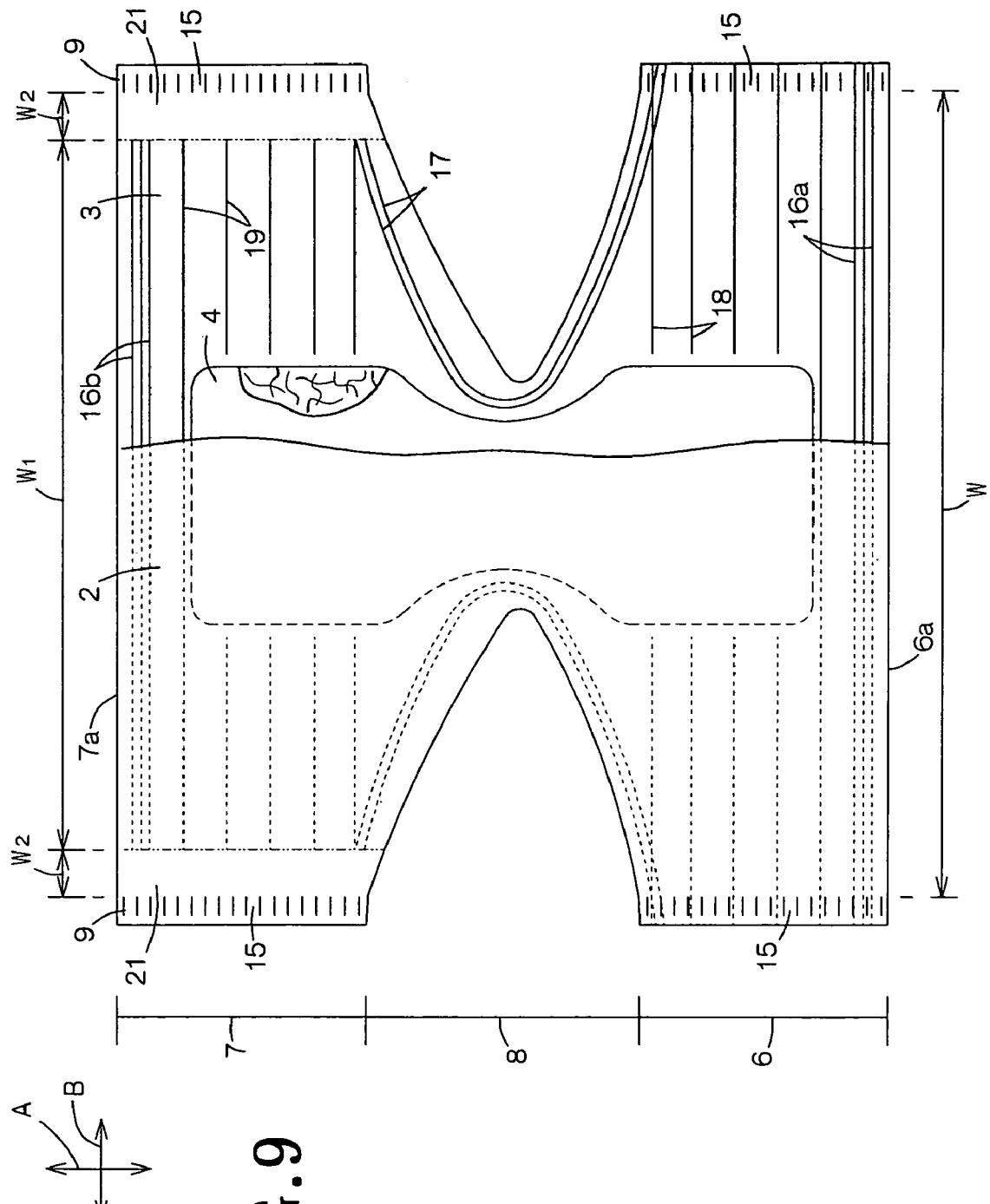
FIG. 9 is a view similar to FIG. 3, showing the diaper of FIG. 8 with front and rear waist regions disconnected from each other and developed in a back-and-forth direction.

FIG. 8 is a view similar to FIG. 1, showing further another embodiment of the invention and FIG. 9 is a view similar to FIG. 3, showing the diaper of FIG. 8 with front and rear waist regions disconnected from each other and developed forward F and rearward R. Unlike the diaper 1 of FIG. 1, in the diaper 1 shown by FIGS. 8 and 9, the rear waist region 7 is formed with a pair of finger-grip zones 21 each having a width $W_2$ and a middle zone 26 extending between these finger-grip zones 21 and having a width $W_1$ while the front waist region 6 has a width W. These dimensions W, $W_1$, $W_2$ in FIGS. 8 and 9 may have the same values as those of the dimensions W, $W_1$, $W_2$. In this diaper 1, stretch- and contractible belly side auxiliary elastic members 18 as well as stretch- and contractile back side elastic members 19 extend in the transverse direction B without extending across the core 4, i.e., these auxiliary elastic members 18, 19 are provided only outside the core 4. In such diaper 1, none of gathers are formed in the core 4 even when the belly side auxiliary elastic members 18 and the back side auxiliary elastic members 19 contract because these auxiliary elastic members 18, 19 extend in stretched state not across the core 4. The diaper 1 having the finger-grip zones 21 provided in the rear waist region 7 advantageously facilitates caregiver to put the diaper 1 on the bedridden patient. This is for the reason that, in the vicinity of the side edges 9 of the rear waist region 7 destined to come near the lateral regions of the patient waist, caregiver can firmly grip the diaper 1.

Figure 10:
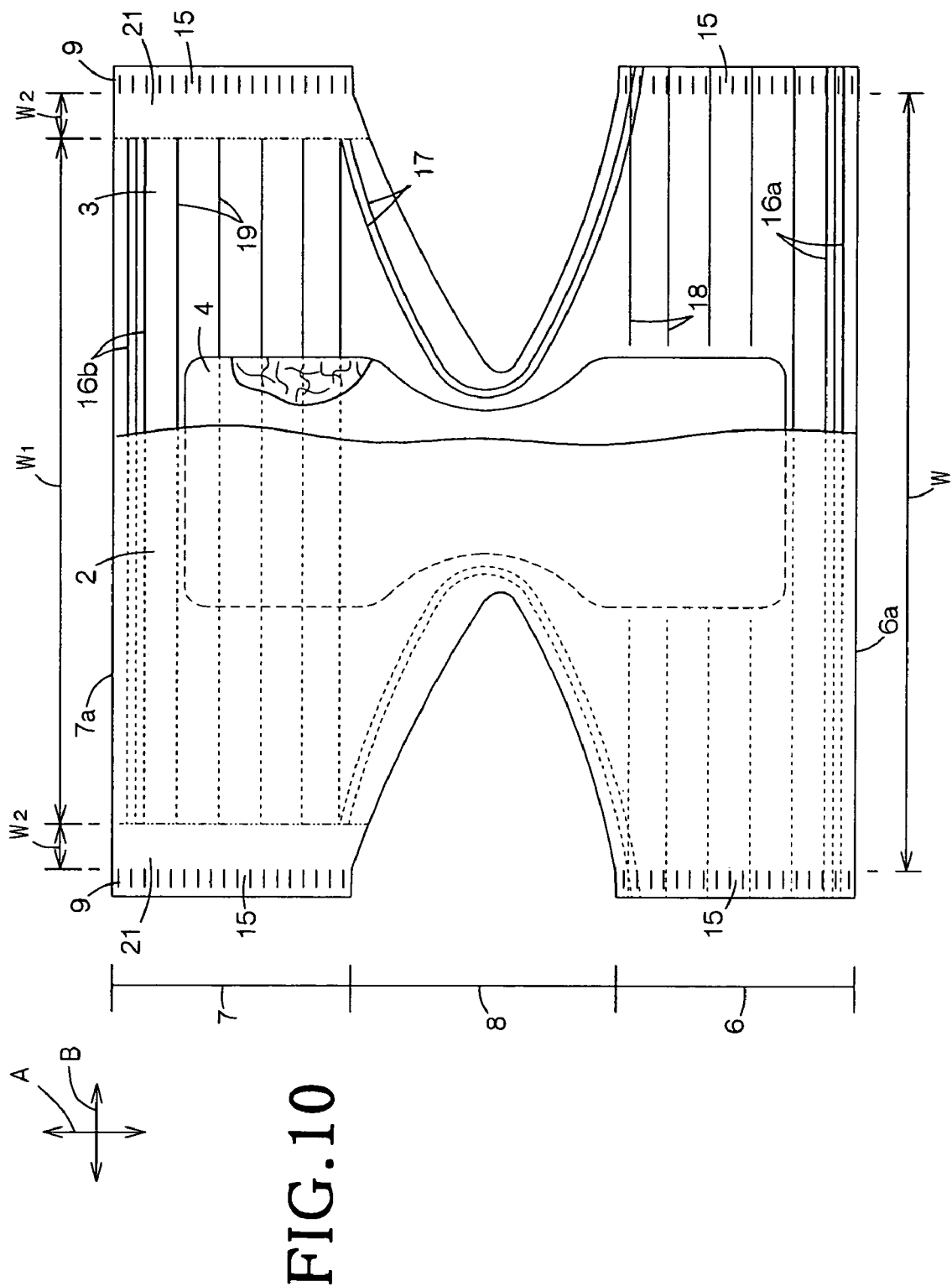
FIG. 10 is a view similar to FIG. 9, showing an alternative embodiment of the invention.

FIG. 10 also is a view similar to FIG. 9, showing an alternative embodiment of the invention. The diaper 1 of FIG. 10 is similar to the diaper 1 shown in FIG. 9 except that the back side auxiliary elastic members 19 extend across the core 4 as the back side auxiliary elastic members 19 in FIG. 3 is the case. In the case of the diaper 1 shown by FIG. 9, the back side auxiliary elastic members 19 extend in the rear waist region 7 between the respective finger-grip zones 21 and the core 4, so these back side auxiliary elastic members 19 are extremely short and apt to press the diaper 1 rather tightly. In contrast with the diaper 1 of FIG. 9, the back side auxiliary elastic members 19 extending across the core as in the diaper 1 of FIG. 10 presses the diaper against the wearer's rear waist region moderately over a large area.

In addition to the pull-on disposable diaper having been described as a specific embodiment, the present invention is applicable to the other pull-on wearing articles such as disposable training pants, sanitary shorts and diaper covers.

What is claimed is:

1. A pull-on disposable wearing article, comprising:
a first waist region, a second waist region and a crotch region extending between said first and second waist regions in a longitudinal direction of said article which further has a transverse direction orthogonal to said longitudinal direction;
side edges of said first waist region opposed to each other in said transverse direction being bonded together with side edges of said second waist region opposed to each other in said transverse direction to form a pair of bonded zones extending in said longitudinal direction;
a waist-hole;
a pair of leg-holes;
said first and second waist regions being elastically stretchable and contractible in said longitudinal direction and said transverse direction or at least in said transverse direction;
said first waist region being elastically stretchable and contractible in said transverse direction over its full range between said bonded zones;
said second waist region comprising:
a pair of finger-grip zones each extending from a peripheral edge of said waist-hole to a peripheral edge of one of said leg-holes and a vicinity thereof, along one of said bonded zones, and over a range of 10 to 100 mm as measured from said bonded zone in the transverse direction, and each of said finger-grip zones being substantially non-stretchable in said longitudinal direction as well as in said transverse direction; and
a middle zone defined between said finger-grip zones and being elastically stretchable and contractible over its full range in said transverse direction;
wherein each said finger-grip zone is a part of the second waist region that is located between and connects the middle zone with the respective one of said bonded zones.

2. The wearing article as defined in claim 1, wherein said finger-grip zones are formed from a sheet material prepared separately from a sheet material used to form said middle zone.

3. The wearing article as defined in claim 1, wherein, in said first and second waist regions, zones other than said finger-grip zones comprise a nonwoven fabric comprising elastic fibers elastically stretchable and contractible in said transverse direction, and
inelastic fibers describing a plurality of loops adapted to be straightened when said nonwoven fabric is stretched in said transverse direction.

4. The wearing article as defined in claim 1, further comprising elastic members that circularly extend along the peripheral edges of said leg-holes so that said elastic members are stretchable and contractible also in said finger-grip zones.

5. The wearing article as defined in claim 1, wherein an entirety of each of said finger-grip zones is located, in the transverse direction, inboard of said bonded zones.

6. The wearing article as defined in claim 5, wherein an entirety of said second waist region in said finger-grip zones is non-stretchable in said transverse direction.

7. The wearing article as defined in claim 1, wherein each of said finger-grip zones has opposite inner and outer sides as seen in the transverse direction, the outer side being adjacent and connected to the respective bonded zone, and the inner side being adjacent and connected to the middle zone.

8. The wearing article as defined in claim 7, wherein an entire thickness of said second waist region in said finger-grip zones is free of elastically stretchable material.

9. The wearing article as defined in claim 1, wherein the respective side edges of said first and second waist regions are permanently bonded together in said bonded zones.

10. The wearing article as defined in claim 1, wherein the peripheral edges of said leg holes are stretchable circumferentially of said leg holes, except in the finger-grip zones.

11. A pull-on disposable wearing article having a longitudinal direction and a transverse direction orthogonal to the longitudinal direction, said article comprising:
a first waist region, a second waist region, and a crotch region extending in the longitudinal direction between said first and second waist regions;
each of said first and second waist regions comprising side edges opposed to each other in said transverse direction;
the side edges of said first waist region being bonded to the respective side edges of said second waist region in a pair of bonded zones to form a waist-hole and a pair of leg-holes;
said first waist region being elastically stretchable and contractible in at least said transverse direction;
said second waist region comprising:
a pair of finger-grip zones each of which is located in the transverse direction between said bonded zones, and is substantially non-stretchable in said transverse direction; and
a middle zone located between said finger-grip zones and being elastically stretchable and contractible in said transverse direction, wherein each of said finger-grip zones extends between and connects the middle zone with one of said bonded zones; and
wherein an entire width of the first waist region between said bonded zones is stretchable in the transverse direction.

12. The wearing article as defined in claim 11, wherein said second waist region has opposite outer and inner surfaces which are adapted to contact, in use, a garment of a user and the user's skin, respectively; and
both the inner and outer surfaces of said second waist region in the finger-grip zones are free of gathers.

13. The wearing article as defined in claim 11, wherein each of said first and second waist regions further comprising an upper edge extending in the transverse direction between said bonded zones, the upper edges of the first and second waist regions together defining a circumferential edge of the waist hole;
the finger-grip zones extend up to the circumferential edge of the waist hole; and
the circumferential edge of the waist hole comprises:
elastic sections which are elastically stretchable and contractible in said transverse direction, and are defined by the upper edge of the second waist region in the middle zone thereof and by the upper edge of the first waist region; and
inelastic sections which are non-stretchable in said transverse direction, and are defined by the upper edge of the second waist region in the finger-grip zones.

14. The wearing article as defined in claim 13, wherein the circumferential edge of the waist hole consists of two said elastic sections and two said inelastic sections which are alternatingly arranged circumferentially of said waist hole; and
wherein the upper edge of the first waist region is free of said inelastic sections.

15. The wearing article as defined in claim 13, wherein the finger-grip zones extend continuously from the circumferential edge of the waist hole in the longitudinal direction up to peripheral edges of the respective leg holes, and partially render the peripheral edges of the respective leg holes non-stretchable in said transverse direction.

16. The wearing article as defined in claim 15, wherein an entirety of said second waist region in said finger-grip zones is non-stretchable in said transverse direction.

17. The wearing article as defined in claim 13, wherein the upper edge of the first waist region defines more than 50% of an entire circumferential length of said waist hole.

18. The wearing article as defined in claim 11, wherein each of said finger-grip zones has opposite inner and outer sides as seen in the transverse direction, the outer side being adjacent and connected to the respective bonded zone, and the inner side being adjacent and connected to the middle zone.

19. The wearing article as defined in claim 18, wherein the respective side edges of said first and second waist regions are permanently bonded together in said bonded zones.

20. The wearing article as defined in claim 19, wherein
said second waist region has opposite outer and inner surfaces which are adapted to contact, in use, a garment of a user and the user's skin, respectively; and
an entire thickness of said second waist region between the outer and inner surfaces in entire said finger-grip zones is free of stretchable material.

21. The wearing article as defined in claim 18, wherein each said finger-grip zone extends seamlessly in the transverse direction from the outer side to the inner side thereof.

22. The wearing article as defined in claim 11, wherein
in each of said bonded zones, a first material of the first waist region is permanently bonded to a second material of the second waist region; and
the first material is elastically stretchable and contractible in said transverse direction whereas as the second material is substantially non-stretchable in said transverse direction.

23. The wearing article as defined in claim 11, wherein the finger-grip zones have a flexural stiffness at least 1.5 times higher than that of the middle zone which extends between and is contiguous to the finger-grip zones.

* * * * *